(12) United States Patent
Herzog et al.

(10) Patent No.: US 6,187,009 B1
(45) Date of Patent: Feb. 13, 2001

(54) OSTEOSYNTHESIS IMPLANT

(75) Inventors: Daniel Herzog, Gelterkinden (CH); Bernhard Kapp, Schopfheim (DE)

(73) Assignee: Synthes (U.S.A.), Paoli, PA (US)

( * ) Notice: Under 35 U.S.C. 154(b), the term of this patent shall be extended for 0 days.

(21) Appl. No.: 09/380,160

(22) PCT Filed: Feb. 28, 1997

(86) PCT No.: PCT/CH97/00074

§ 371 Date: Nov. 8, 1999

§ 102(e) Date: Nov. 8, 1999

(87) PCT Pub. No.: WO98/37825

PCT Pub. Date: Sep. 3, 1998

(51) Int. Cl.[7] ................................................. A61B 17/68
(52) U.S. Cl. ................ 606/75; 606/232; 606/72
(58) Field of Search .................. 606/75, 76, 77, 606/72, 60, 232; 411/450, 456, 458, 459, 460

(56) References Cited

U.S. PATENT DOCUMENTS

| 4,454,875 | * | 6/1984 | Pratt et al. | 411/457 |
|---|---|---|---|---|
| 5,236,431 | * | 8/1993 | Gogolewski et al. | 606/72 |
| 5,275,601 | * | 1/1994 | Gogolewski et al. | 606/72 |
| 5,454,814 | * | 10/1995 | Comte | 606/75 |
| 5,643,261 | * | 7/1997 | Schafer et al. | 606/72 |
| 5,779,707 | * | 7/1998 | Bertholet et al. | 606/75 |
| 5,785,713 | * | 7/1998 | Jobe | 606/75 |
| 5,968,078 | * | 10/1999 | Grotz | 606/232 |
| 6,013,077 | * | 1/2000 | Harvin | 606/72 |

* cited by examiner

Primary Examiner—Pedro Philogene
(74) Attorney, Agent, or Firm—Pennie & Edmonds LLP

(57) ABSTRACT

The osteosynthesis implant according to the present invention includes a base body in the form of a plate having an upper side and a lower side intended for contact with the bone. The lower side has extensions for insertion in the bone, and their outer surface is provided with a retaining structure. The entire implant is made of an bioabsorbable material. The bone fragments to be secured can be joined easily and reliably with the implant according to this invention and no explantation is necessary after osteosynthesis.

28 Claims, 3 Drawing Sheets

OSTEOSYNTHESIS IMPLANT

FIELD OF THE INVENTION

This invention concerns an implant for osteosynthesis for joining bone fragments.

BACKGROUND OF THE INVENTION

Such implants for osteosynthesis are already known from the state of the art, in particular those made of memory alloys and those from ordinary metal alloys but with an elastic prestress. The disadvantages of these known implants include the fact that neither type (memory alloys and non-memory alloys) is bioabsorbable and therefore a second surgery is potentially necessary to remove the metal. In addition, the biocompatibility of memory alloys is disputed due to their high nickel content. Because of the fact that the metal implant must be removed subsequently, their extensions cannot be provided with a retaining structure either. Finally, another disadvantage of the known implants is that they have only two extensions.

International Patent WO-A 9526164 discloses an implant for osteosynthesis for joining bone fragments. However, a disadvantage of this known implant is the considerable and constant thickness of the plate-shaped base body.

SUMMARY OF THE INVENTION

The object of this invention is to create an implant for osteosynthesis, in particular for the maxillofacial area, to which the bone parts to be secured can be joined easily and reliably and which need not be explanted after successful osteosynthesis.

The osteosynthesis implant according to the present invention includes a body having an upper side and a lower side for contact with bone and first and second extensions attached to the lower side of the body for implantation in bone. Each of the first and second extensions has an outer surface with a plurality of retaining members for securement in bone. The implant is made of a bioabsorbable material and the body has a thickness that decreases from the center to the periphery.

This invention yields the advantage that in the case of a single implant having multiple extensions, a multi-fragment fracture (e.g., in the skull area) can be treated with just one component. In the case of a simple fracture (with only one fracture line), the stability of the fracture repair can be increased significantly by a single implant. Finally, another advantage is that the operation time is greatly shortened in comparison with known implants.

In one embodiment the extensions of the implant are not perpendicular to the base body but instead converge toward one another, thus resulting in a prestress on these extensions. The prestress thus created then causes a minimal compression on the fracture and thus shortens the bone regeneration time. The maximum angle is preferably 20°.

To be able to use the implant according to this invention optimally, it is important for the bone fragments to be repositioned without any gaps. In order to ensure this, the holes for the extensions of the implant to be inserted into the bone are predrilled by means of a multiple drilling head which is placed over the fracture line so that all the required holes can be created in a single operation. Then the implant is held by means of a suitable instrument which neutralizes any convergence of the extensions (i.e., the extensions are aligned in parallel by means of the instrument), so that the implant can then be pressed into the parallel aligned "multiple holes" and secured there. Then any retention aid attached there can be removed.

The prestress produced by the convergent extensions causes a minimal compression on the fracture and can thus promote regeneration of the bone. In addition, the prestress together with the retaining structure of the extensions ensures a better hold of the implant of the bone.

In another preferred embodiment, the extensions of the implant are designed as hollow bodies with a central channel into which a spreading body can be inserted to achieve even better fixation.

In addition to the main use of the implant according to this invention for bridging fracture gaps, it can also be used as a fixation component for absorbable films, membranes or absorbable osteosynthesis plates.

The films or membranes are used mainly to bridge bone defects, reconstruct the eye socket, and achieve controlled osteogenesis in the dental area.

BRIEF DESCRIPTION OF THE DRAWINGS

This invention and refinements of this invention are explained in greater detail below on the basis of the partially schematic diagrams of several embodiments.

They show.

DETAILED DESCRIPTION OF THE PREFERRED EMBODIMENTS

Figure 1:
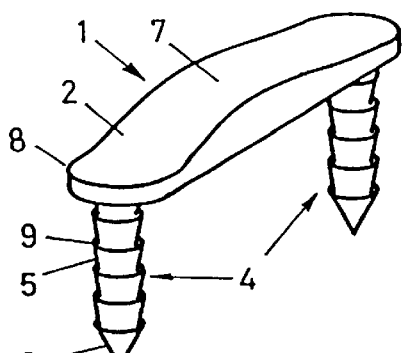
FIG. 1: a perspective view of an implant according to this invention with two extensions.
Figure 2:
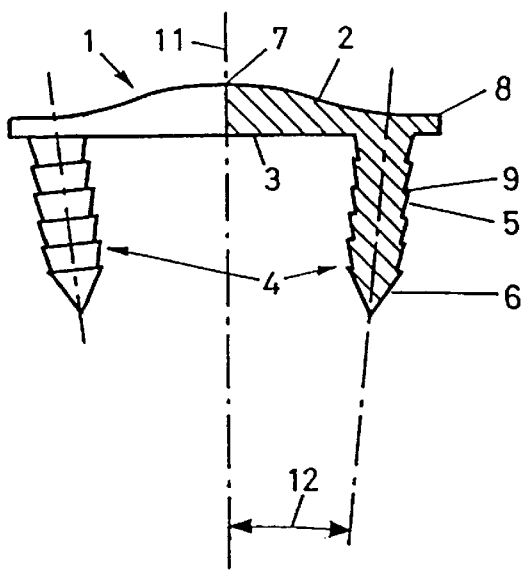
FIG. 2: a longitudinal section through the implant according to FIG. 1.

The implant according to this invention illustrated in FIGS. 1 and 2 consists essentially of a base body 1 in the form of a plate having a vaulted upper side 2 and a planar lower side 3 intended for contact with the bone.

The base body 1 in the form of a plate, e.g., rectangular, may be designed to be either solid or a mesh, with the thickness of the plate-shaped base body 1 decreasing continuously from the center 7 toward the periphery 8.

The lower side 3 of the implant has two extensions 4 which are intended for implantation in the bone and whose outer surfaces 5 are provided with a retaining structure 9 in the form of truncated conical sections which widen in the form of a cone toward the lower side 3.

The extensions 4 which are in the form of circular cylinders converge toward one another and form an angle 12 of 1° to 15°, preferably 2° to 10° to the perpendicular 11 to the base body 1. The extensions 4 are pointed at their free end.

The entire implant consists of a bioabsorbable material which has the following properties:
  retaining the initial stability over a period of six to eight weeks;
  plastic deformability under the influence of heat; and
  swellability of the implant after implantation.

Figure 3:
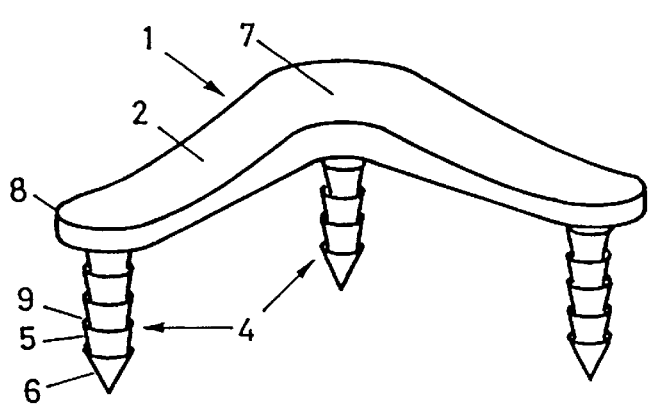
FIG. 3: a perspective view of an implant according to this invention with three extensions.

FIG. 3 shows another embodiment of the implant according to this invention in the form of an angle plate with three extensions 4. In this embodiment, the extensions 4 designed in the form of circular cylinders are essentially perpendicular to the base body 1 and are rounded on their free end 6.

Figure 4:
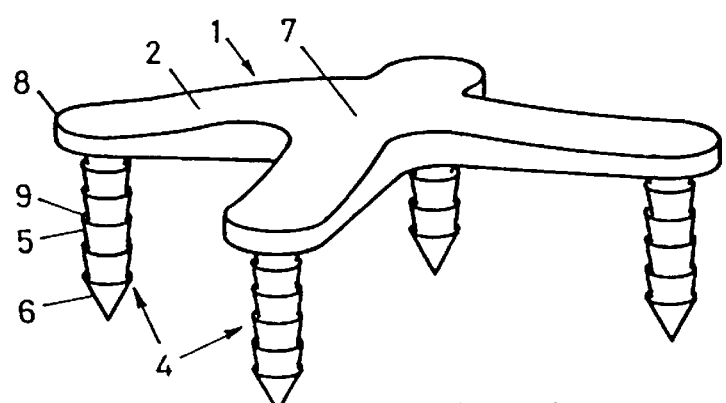
FIG. 4: a perspective view of an implant according to this invention with four extensions.

FIG. 4 shows another embodiment of the implant according to this invention in the form of a star with four extensions 4, one on each of the free star points. In this embodiment, the extensions 4 which are designed in the form of circular cylinders are essentially perpendicular to the base body 1 and are rounded on their free end 6.

Figure 5:
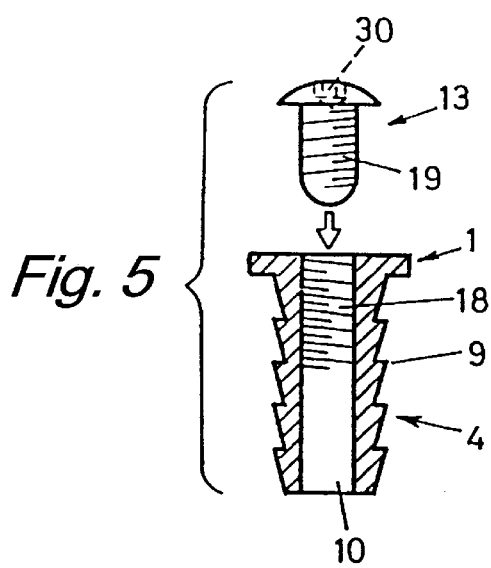
FIG. 5: a longitudinal section through the extension of an implant according to this invention with a spreading body.

As shown in FIG. 5, the extension 4 may be designed as a hollow body with a central channel 10 into which a spreading body 13, preferably bioabsorbable, can be inserted to spread the extension 4 with its retaining structure 9 in the bone. The spreading body 13 is preferably designed as a screw with an outside thread 19 which can be screwed into the inside thread 18 of the central channel 10. For this purpose, the head of the spreading body 13 is provided with a hexagonal socket 30 into which a suitable screw driving instrument can be inserted.

Figure 6:
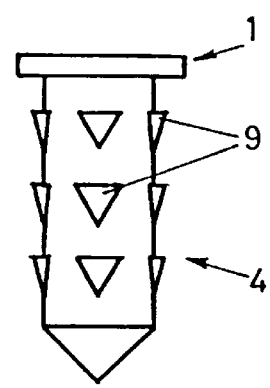
FIG. 6: a side view of a modified extension with barbs.
Figure 7:
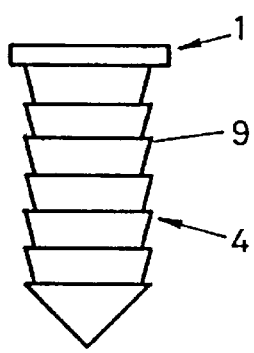
FIG. 7: a side view of another variant of an extension with truncated conical sections.

As shown in FIG. 6, the retaining structure 9 may also consist of barbs directed toward the lower side 3 in all embodiments.

Figure 8:
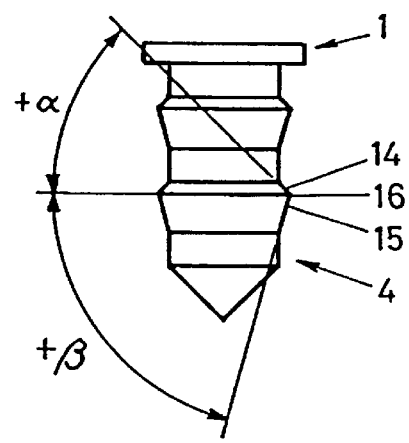
FIG. 8: a side view of another variant of an extension with sawteeth.
Figure 9:
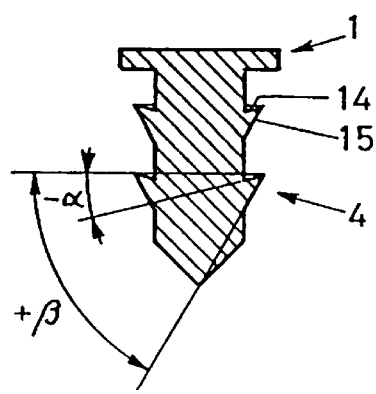
FIG. 9: a longitudinal section through another variant of an extension with a longitudinal slot.
Figure 10:
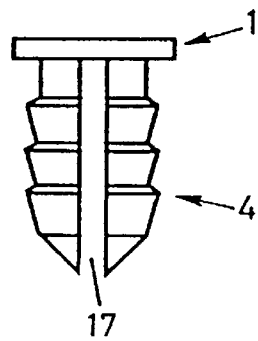
FIG. 10: a perspective view of an implant according to this invention with extensions having central channels and a closing part which fits it.

FIGS. 8 through 10 show variants of the extensions 4 which have sawteeth 16 as a retaining structure.

In the variant shown in FIG. 8, the angle α formed by the surface 14 of the sawteeth 16 directed toward the base body 1 with the plane of the base body 1 has a positive value, whereas in the variant illustrated in FIG. 9, the angle α has a negative value.

In both cases, the absolute value of the angle α is less than or at most equal to that of the angle +β formed by the surface 15 of the sawteeth 16 directed toward the free end 6 with the plane of the base body 1.

FIG. 10 shows a variant of the extensions 4 with a longitudinal slot 17 to facilitate spreading in the bone. The longitudinal slots 17 may be designed to be open at the lower end, as shown in FIG. 10, or closed at the lower end.

Figure 11:
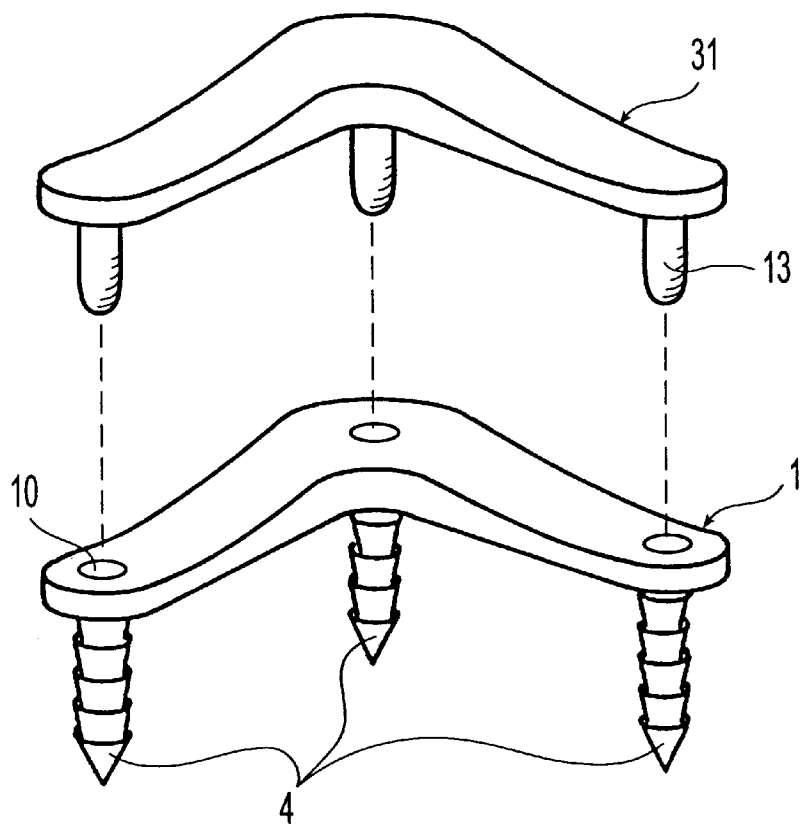
FIG. 11: a perspective view of an implant according to this invention with three extensions.

Finally, FIG. 11 shows an implant 1 which has three extensions 4 having a central channel 10. The central channels 10 may be closed at the same time by means of the closing part 31, which has three interconnected spreading bodies 13.

What is claimed is:

1. An osteosynthesis implant comprising:
  a body with a center and a periphery and having a vaulted upper side and a lower side for contact with bone, a thickness of the body decreasing from the center to the periphery; and
  first and second extensions attached to the lower side of the body for implantation in bone, each of the first and second extensions having an outer surface with a plurality of retaining members for securement in bone, wherein the implant is made of a bioabsorbable material.

2. The implant of claim 1 wherein the first and second extensions are perpendicular to the body.

3. The implant of claim 1 wherein the first and second extensions converge toward one another.

4. The implant of claim 3 wherein each of the first and second extensions forms an angle of less than around 20° with respect to a line normal to the lower side of the body.

5. The implant of claim 1 wherein each of the first and second extensions has a substantially cylindrical shape and a distal end with a tip.

6. The implant of claim 1 wherein each of the retaining members has a sawtooth shape with a first surface forming a first angle with a plane parallel to the lower side of the body and a second surface forming a second angle with a plane parallel to the lower side of the body, the first surface being closer to the lower side of the body than the second surface.

7. The implant of claim 6 wherein the absolute value of the first angle is less than or equal to the absolute value of the second angle.

8. The implant of claim 6 wherein the first angle is about 0°.

9. The implant of claim 6 wherein the first angle is positive.

10. The implant of claim 6 wherein the first angle is negative.

11. The implant of claim 1 wherein each of the retaining members is a barb.

12. The implant of claim 1 wherein each of the retaining members is a truncated conical section widening towards the lower side of the body.

13. The implant of claim 1 wherein the body is a mesh.

14. The implant of claim 1 wherein the body has a substantially rectangular shape and the first extension is attached to a first end of the lower side of the body and the second extension is attached to second end of the lower side of the body.

15. The implant of claim 1 further comprising a third extension attached to the lower side of the body for implantation in bone and having an outer surface with a plurality of retaining members for securement in bone and wherein the body has a boomerang shape with the first extension attached to a first end of the lower side of the body, the second extension attached to second end of the lower side of the body, and the third extension attached under the center of the body.

16. The implant of claim 1 further comprising third and fourth extensions attached to the lower side of the body for implantation in bone, each of the third and fourth extensions having an outer surface with a plurality of retaining members for securement in bone, wherein the body has a star shape.

17. The implant of claim 1 wherein each of the first and second extensions has a hollow interior with a central channel.

18. The implant of claim 17 wherein each of the central channels is closed at a lower end.

19. The implant of claim 17 wherein each of the central channels is open at a lower end.

20. The implant of claim 17 wherein each of the central channels has a constant cross section.

21. The implant of claim 17 wherein each of the central channels has a cross section that tapers toward a lower end.

22. The implant of claim 17 wherein each of the central channels has a cross section that tapers toward an upper end.

23. The implant of claim 17 wherein at least a portion of each of the central channels is threaded.

24. The implant of claim 23 further comprising first and second spreading bodies, each of the spreading bodies having a head and a stem insertable in one of the central channels for expanding the respective extension.

25. The implant of claim 24 wherein the stem of each of the spreading bodies is threaded and the head of each of the spreading bodies has a recess for coupling with a driver to insert the spreading body in the respective central channel.

26. The implant of claim 24 wherein each of the spreading bodies is made of a bioabsorbable material.

27. The implant of claim 17 further comprising a closing part with a base connecting first and second prongs, each of the prongs configured and dimensioned for insertion in one of the first and second extensions to expand the respective extension.

28. The implant of claim 17 wherein at least one of the first and second extensions has a longitudinal slot for allowing the extension to spread upon insertion in bone.

* * * * *